United States Patent [19]

Mauvernay et al.

[11] 4,029,790
[45] June 14, 1977

[54] 1-BENZOYL-2 OR 4 [2-(4-PHENYL-PIPERAZINO)-ETHYL]-PIPERIDINES

[75] Inventors: Roland Yves Mauvernay, Riom; Norbert Busch, Loubeyrat; Jacques Moleyre, Mozac; Jacques Simond, Chamalieres; André Monteil, Gerzat, all of France

[73] Assignee: Centre European de Recherches Mauvernay, Riom, France

[22] Filed: Sept. 26, 1975

[21] Appl. No.: 617,141

[30] Foreign Application Priority Data

Sept. 30, 1974 France .................. 74.32805

[52] U.S. Cl. ................... 424/250; 260/268 PH
[51] Int. Cl.² ............. A61K 31/495; C07D 401/06
[58] Field of Search ............. 424/250; 260/268 C, 260/268 PH

[56] References Cited

UNITED STATES PATENTS 3,729,474  4/1973  Mentrup et al. ............ 260/268 BC
3,753,985  8/1973  Gavin et al. ................ 260/268 BC Primary Examiner—Donald G. Daus
Assistant Examiner—Jose Tovar

[57] ABSTRACT

Compounds of the formula

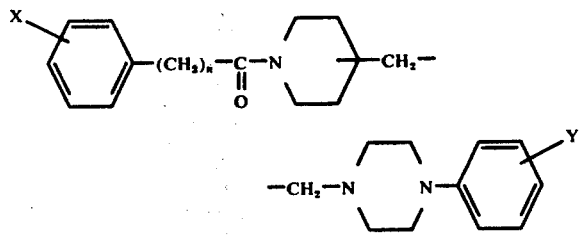

and pharmaceutically acceptable acid salts thereof, wherein X is hydrogen, halogen or methoxy, $n$ is zero, Y is halogen and the ethyl piperazaine moiety is attached to the 2- or 4- position of the piperidine ring, is described. These compounds have anti-spasmolytic and antitussive activity.

9 Claims, No Drawings

1-BENZOYL-2 OR 4 [2-(4-PHENYL-PIPERAZINO)-ETHYL]-PIPERIDINES

This invention is concerned with new piperidine derivatives, the preparation thereof, and pharmaceutical compositions containing them.

It has now been found, in accordance with the present invention, that certain piperidine derivatives, as hereinafter defined, possess bronchospasmolytic activity.

According to the invention, therefore, there are provided as new compounds, compounds of the general formula:

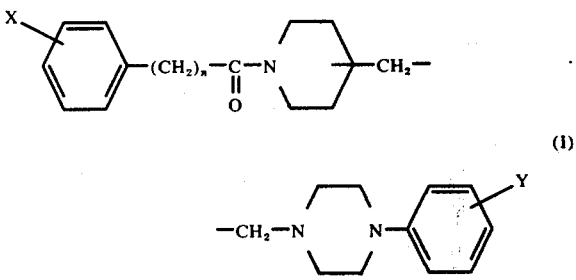

In which X and Y each represent a hydrogen or halogen atom or an alkyl or alkoxy groups, $n$ is 0 or 1, and the ethylpiperazine moiety is attached to the 2- or 4-position of the piperidine ring.

The invention also relates to a three stage process for the preparation of the compounds defined above starting from a vinylpiperidine (preferably 2- or 4-piperidine). The intermediate obtained in the second stage of this process is, itself, new and is provided as a further feature of the invention.

The invention is also concerned with the use of the new compounds in therapy in view of their bronchospasmolytic activity and, accordingly, also relates to pharmaceutical compositions containing the new compounds.

In French BSM Patent No. 8436 M we have already described compounds having a general structure similar to those of the compounds in accordance with the present invention, namely having the general formula:

In which Ar and Ar₁ represent aryl or aralkyl residues. These compounds possess antihistaminic and antiallergic properties. The general structure of the compounds of the present invention differs from that of those of formula II in that the same general arrangement of active sites (nitrogen atoms and carbonyl groups) is spacially disposed in a different manner due to the presence of the piperidine ring, that is because of the inclusion of a nitrogen atom in the heterocycle.

It has been possible to obtain compounds in accordance with the present invention having this different structure by the use of a new process which consists, basically, of, firstly, condensing a vinyl pyridine with an N-phenyl piperazine in known manner, secondly selectively reducing the pyridine nucleus to a piperidine nucleus by catalytic hydrogenation in the presence of rhodium supported on active carbon (5% rhodium), and finally amidifying the product obtained in the second stage by reaction with a suitable acid chloride.

The three stages of the process in accordance with the invention may be summarised by the following reaction scheme:

1st Stage

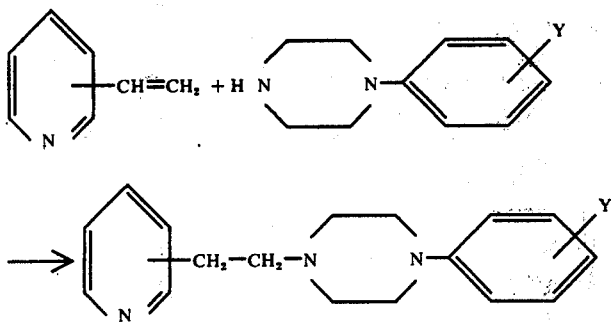

2nd Stage

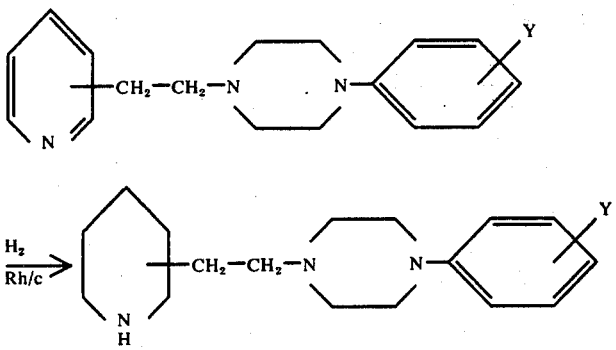

3rd Stage

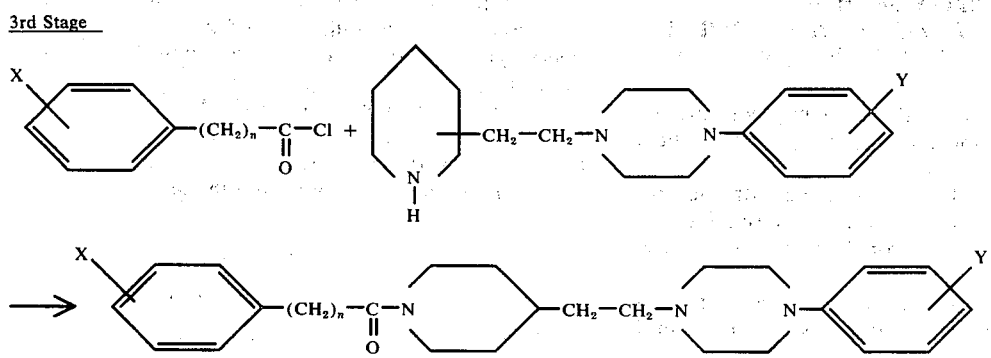

The compound obtained in the 2nd stage is itself new and is a necessary intermediate for the present synthesis and is further provided as a feature of the invention.

The process of the invention is described in more detail with reference to the two following Examples:

EXAMPLE 1

Synthesis of 1-(4-fluoro)-benzoyl-2-{2-[4-(4-fluoro)phenyl] piperazinyl} ethyl piperidine 1st Stage 52 g of freshly distilled 2-vinyl pyridine are added to a solution of 90 g (0.5 mole) of para-fluorophenyl-piperazine in 250 ml of absolute ethanol and 30 g of acetic acid. The mixture is refluxed for 4 hours after which the solvent is evaporated off. The residue is taken up in 500 ml of water and neutralised with sodium hydroxide solution. After extraction with chloroform, drying and evaporation the product crystallises to give 134 g (94% theoretical) of a compound melting at 92° C.

2nd Stage 70 g (0.25 mole) of the product obtained in the first stage are dissolved in 500 ml of alcohol at 96° C and acidified with concentrated hydrochloric acid. The solution is introduced into a hydrogenation flask together with 7 g of rhodium supported on active carbon (5% rhodium).

After stirring for 8 hours under a hydrogen pressure of 40 p.s.i. the catalyst is filtered off and the alcohol is evaporated off. The resultant hydrochloride is recrystallised from ethanol to give 70 g (yield about 70% of a product having a melting point of 285° C and the following analysis:

|  | C% | H% | N% |
|---|---|---|---|
| Calculated | 50.94 | 7.29 | 10.48 |
| Found | 49.40 | 9.28 | 10.85 |

The free base is obtained by treatment with concentrated sodium hydroxide solution: the product thus obtained is obtained pasty form and is used as such in the following stage.

3rd Stage 14.5 g (0.05 mole) of the product obtained in the second stage are dissolved in 200 ml of anhydrous benzene and there are added thereto 10 ml of triethylamine. 13 g (0.08 mole) of parafluorobenzoyl chloride are added to the cooled solution dropwise, the reaction mixture is allowed to return to ambient temperature and it is allowed to stand overnight.

The precipitate is filtered off, the solution is evaporated, taken up in chloroform, and then washed with water, followed by water saturated with sodium carbonate and finally with water. After drying and evaporation the hydrochloride is made in an alcoholic medium to give about 15 g of product (63% theoretical).

EXAMPLE 2

Synthesis of 1-(4-chloro)benzolyl-4-{2-[4-(4-chloro)phenyl]-piperazinyl}-ethyl piperidine 1st Stage 52 g of freshly distilled 4-vinyl pyridine are added to a solution of 98 g (0.05 mole) of parachlorophenyl piperazine in 250 ml of absolute ethanol and 30 g of acetic acid. The mixture is then refluxed for 10 hours. The solvent is evaporated off and the residue taken up in 500 ml of water and neutralised with concentrated sodium hydroxide solution. After extraction with chloroform, drying and evaporation the crude product is obtained in the form of a paste usable as such in the following stage. The yield is 140 g (100% theoretical).

2nd Stage

75 G (025 mole) of the base obtained in the first stage are dissolved in 600 ml of 96° alcohol and acidifed with concentrated hydrochloric acid. 7.5 g of rhodium supported on active carbon (5% rhodium) are added to the mixture which is then hydrogenated under a pressure of 40 p.s.i. The consumption of hydrogen is complete at the end of about 40 hours.

After filtering off the catalyst, the alcohol is evaporated off and the residue taken up in water and neutralised with concentrated sodium hydroxide solution. After extraction there are obtained 45 g of product (60% theoretical).

3rd Stage

Amidification with parachlorobenzoyl chloride 15.75 g (0.05 mole) of the compound obtained in the 2nd stage are dissolved in 200 ml of anhydrous benzene in the presence of 10 ml of triethylamine. 16 g (0.08 mole) of parachlorobenzoyl chloride are added dropwise to the solution cooled to 6° C. The reaction mixture is then allowed to stand overnight at ambient temperature. The precipitate is filtered off and the filtrate concentrated and taken up in chloroform. The chloroformic solution is washed with water, then with water saturated with sodium carbonate and finally with water. After evaporation the trihydrochloride precipitate is precipitated by reaction with ethanol saturated with hydrogen chloride to give, after recrystallisation, 13 g of product (55% theoretical).

Table 1 below gives the characteristics of other compounds which have been prepared by the procedure indicated above. For clarity the compounds have been separated according to whether the substitution on the piperidine nucleus is in the 2- or 4-position.

In all the Examples the X in the phenyl group is in the para position.

route, 45 minutes after treatment, they were again subjected to the aerosol. The animals resisting the aerosol for 10 minutes longer than previously were considered as being protected by the treatment. The product under test was administered to lots of 10 animals. In the first test the dose used was 50 mg/kg P.O. If the product was found to be active the dosages were reduced in order to establish the $ED_{50}$ by the linearisation method.

TABLE 1

| Compound No. | n | X | (Piperidine substituted in 2-position) | | | | | | C | H | N |
| | | | Y | MW | Salt | m.p. | | | | | |
|---|---|---|---|---|---|---|---|---|---|---|---|
| 1 | 0 | H | p.F. | 468.46 | 2HCl | 218° C | % th | | 61.53 | 6.88 | 8.97 |
| | | | | | | | % f | | 60.98 | 7.00 | 8.8 |
| 2 | 0 | Cl | p.F. | 502.91 | 2HCl | 220° C | % th | | 57.32 | 6.21 | 8.35 |
| | | | | | | | % f | | 57.20 | 6.43 | 8.37 |
| 3 | 1 | H | p.F. | 482.48 | 2HCl | 209° C | % th | | 62.23 | 7.10 | 8.71 |
| | | | | | | | % f | | 61.98 | 7.42 | 8.67 |
| 4 | 0 | F | p.F. | 486.450 | 2HCl | 216° C | % th | | 59.26 | 6.42 | 8.64 |
| | | | | | | | % f | | 59.37 | 6.26 | 8.59 |
| 5 | 0 | Cl | p.Cl | 519.36 | 2HCl | 193° C | % th | | 55.5 | 6.02 | 8.09 |
| | | | | | | | % f | | 54.9 | 6.3 | 8.12 |
| 6 | 0 | F | p.Cl | 502.91 | 2HCl | 239° C | % th | | 57.32 | 6.21 | 8.35 |
| | | | | | | | % f | | 58.0 | 6.19 | 8.40 |
| 7 | 0 | H | p.Cl | 484.91 | 2HCl | 210° C | % th | | 59.45 | 6.65 | 8.67 |
| | | | | | | | % f | | 58.90 | 6.74 | 8.71 |
| 8 | 0 | OCH₃ | p.F. | 498.48 | 2HCl | 204° C | % th | | 60.23 | 6.87 | 8.43 |
| | | | | | | | % f | | 59.65 | 6.44 | 8.45 |
| 9 | 0 | Cl | m.Cl | 482.90 | 1HCl | 226° C | % th | | 59.69 | 6.26 | 8.70 |
| | | | | | | | % f | | 59.23 | 6.36 | 8.61 |

| Compound No. | n | X | (Piperidine substituted in 4-position) | | | | | | C | H | N |
| | | | Y | MW | Salt | m.p. | | | | | |
|---|---|---|---|---|---|---|---|---|---|---|---|
| 10 | 0 | Cl | p.Cl | 519.36 | 2HCl | 216° C | % th | | 55.5 | 6.02 | 8.09 |
| | | | | | | | % f | | 56.2 | 6.22 | 8.13 |
| 11 | 0 | H | p.Cl | 484.91 | 2HCl | 200° C | % th | | 59.45 | 6.65 | 8.67 |
| | | | | | | | % f | | 60.05 | 6.67 | 8.84 |
| 12 | 0 | F | p.Cl | 446.44 | 1HCl | 160° C | % th | | 71.8 | 6.48 | 9 |
| | | | | | | | % f | | 61.55 | 6.70 | 8.93 |
| 13 | 0 | Cl | p.F. | 502.91 | 2HCl | 227° C | % th | | 57.32 | 6.21 | 8.35 |
| | | | | | | | % f | | 56.95 | 6.44 | 8.27 |
| 14 | 0 | F | p.F. | 486.45 | 2HCl | 218° C | % th | | 59.26 | 6.42 | 8.64 |
| | | | | | | | % f | | 58.42 | 6.73 | 8.70 |
| 15 | 0 | OCH₃ | p.F. | 498.48 | 2HCl | 203° C | % th | | 60.23 | 6.87 | 8.43 |
| | | | | | | | % f | | 60.56 | 7.02 | 8.40 |

The bronchospasmolytic and also antitussive activities of these compounds were investigated by means of the following tests:

1. Histaminic bronchospasm in the Guinea Pig

The histamine aerosol technique was used.

The guinea pigs, or either sex and weighing from 250 to 400 g. were placed in an enclosure through which circulated a 0.3% aerosol of histamine in a mixture of distilled water and 20% glycerine.

The animals were removed from the enclosure when they succumbed to asphyxic syncope and the time of exposure was noted. This value serves as a control value, since, 24 hours later, the same animals were treated with the compounds under test by the oral 2. Investigation of Antitussive Properties in the Cat The test used was then of Domenjoz R.(Arch. Exp. Pathol. v. Pharmacol. 215, 1952).

The electrical stimulation of the upper laryngic nerve had the following characteristics: 2v, 6 Hz square waves of 5 msec - period of stimulation 10 to 20 seconds at intervals of 7 minutes 5 seconds. The activity of the product was evaluated as a percentage of inhibition.

Table II below gives the results obtained in the two above tests with certain compounds in accordance with the invention.

TABLE II

| | BRONCHOSPASMOLYTIC ACTIVITY | | | ANTITUSSIVE ACTIVITY | | |
| | 50 mg/kg P.O. | | | Dose | | |
| Compound No. | activity % | N | $ED_{50}$ (mg/kg P.O.) | mg/kg I.D. | N | Mean |
|---|---|---|---|---|---|---|
| 1 | 60 | 10 | — | 10 | 3 | 73.7 ± 13.7 |
| 2 | 100 | 10 | 25 | 10 | 3 | 0 |
| 4 | 100 | 10 | 5.7]3.8/8.5[ | 10 | 5 | 58.6 ± 19.2 |
| 7 | 60 | 10 | | 20 | 2 | 74 |
| 9 | 80 | 10 | 13] 6.0 − 27.9[ | | | |
| 10 | 100 | 5 | | 20 | 3 | 0 |
| 12 | 70 | 10 | 30.9] 20 − 47.6[ | 20 | 3 | 0 |
| 13 | 100* | 10 | 11.6] 9.1/14.0[ | 20 | 2 | 0 |
| 14 | 100* | 10 | 0.94] 0.5/1.6[ | 20 | 3 | 44.7 ± 29.3 |
| Dextromethorphane | 0*** | 10 | | 10 | 5 | 76.2 ± 34.0 |
| Diphenyl- | 93 | 15 | 4.5] 3.4/5.9[ | 10 | 6 | 65.3 ± 9.5 |

TABLE II-continued

| Compound No. | BRONCHOSPASMOLYTIC ACTIVITY | | | ANTITUSSIVE ACTIVITY | | |
|---|---|---|---|---|---|---|
| | 50 mg/kg P.O. activity % | N | $ED_{50}$ (mg/kg P.O.) | Dose mg/kg I.D. | N | Mean |
| dramine | 10 mg/kg | | | | | |

$ED_{50}$: Effective dose 50 calculated by the linearisation method
] [: 5% confidence limit of $ED_{50}$
\*: Dose used : 25 mg/kg P.O.
\*\*: Dose used : 100 mg/kg P.O.
N: Number of animals.

These results show, from a majority of the compounds, an affinity for the bronchopulmonary system; the activities particularly marked for Compounds Nos. 2, 4, 13 and 14, Compound No. 1 possessing other interesting antitussive properties.

All the compounds have low toxicities. Thus the $LD_{50}$ by the oral route in the mouse as determined by the method of Behrens and Karber (Arch. F. Exp. Path. Parm. 177, 389, 1935) lies between 300 and 600 mg/kg.

The compounds of the invention, are associated with conventional pharmaceutical excipients, may be envisaged for use in the therapy or treatment of conditions of the bronchopulmonary system at daily doses of between 10 and 500 mg.

Accordingly, another embodiment of the invention provides a pharmaceutical composition comprising a compound in accordance with the invention in association with a pharmaceutical carrier or diluent. Such compositions are preferably in the form of orally administrably compositions, such as tablets, dragees, capsules or the like, and may contain doses of active ingredient of from 5 to 200 mg, preferably from 10 to 100 mg.

What we claim is:

1. A compound of the formula:

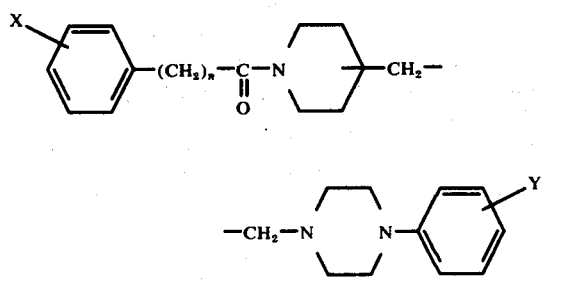

(1)

and salts thereof with pharmaceutically acceptable acids in which X represents a hydrogen or halogen atom or methoxy group, n is 0; Y represents a halogen atom; and the ethyl piperazine moiety is attached to the 2- or 4- position of the piperidine ring.

2. 1-Benzoyl 2- {2-[4-(4-fluoro)phenyl)piperazinyl} ethyl piperidine.

3. 1-(4-Chloro)benzoyl 2- {(2-[4-(4-fluoro)phenyl] piperazinyl} ethyl piperidine.

4. 1-(4-Fluoro)benzoyl 2- {2-[4-(4-fluoro)phenyl]- piperazinyl} ethyl piperidine.

5. 1-(4-Chloro)benzoyl 4- {2-[ 4-(4-chloro)phenyl]- piperazinyl} ethyl piperidine.

6. 1-(4-Chloro)benzoyl 4- {2-[4-(4-fluoro)phenyl]- piperazinyl} ethyl piperidine.

7. 1-(-Fluoro)benzoyl 4- {2[ 4-[ 4-fluoro)phenyl]- piperzinyl} ethyl piperidine.

8. A pharmaceutical composition consisting essentially of a compound of

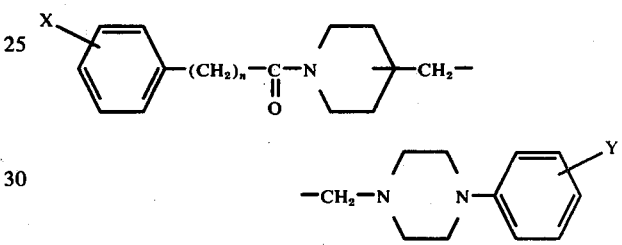

and salts thereof with pharmaceutically acceptable acids in which X represents a hydrogen or halogen atom or a lower alkoxy group, n is 0; Y represents a halogen atom; and the ethyl piperazine moiety is attached to the 2- or 4- position of the piperidine ring in association with a pharmaceutically acceptable carrier or diluent.

9. A method of treating bronchospasmolytic and tussive conditions by administering a formula:

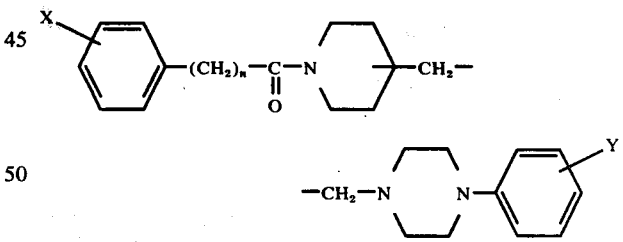

or pharmaceutically acceptable acid salts thereof in which X represents a hydrogen or halogen atom or methoxy group, n is 0; Y represents a halogen atom; and the ethyl piperazine moiety is attached to the 2- or 4- position of the piperidine ring in dosages of from 10 to 500 mg per day in an orally acceptable form.

* * * * *

UNITED STATES PATENT AND TRADEMARK OFFICE
CERTIFICATE OF CORRECTION

PATENT NO. : 4,029,790

DATED : June 14, 1977

INVENTOR(S) : MAUVERNAY ET AL

It is certified that error appears in the above-identified patent and that said Letters Patent are hereby corrected as shown below:

On the cover sheet change "Centre European" to

--Centre Europeen--

Signed and Sealed this

Tenth Day of January 1978

[SEAL]

Attest:

RUTH C. MASON
*Attesting Officer*

LUTRELLE F. PARKER
*Acting Commissioner of Patents and Trademarks*